US008741652B2

(12) United States Patent
Siddavattam et al.

(10) Patent No.: US 8,741,652 B2
(45) Date of Patent: Jun. 3, 2014

(54) GENETICALLY TRANSFORMED MICROORGANISMS WITH SIMULTANEOUS ENHANCEMENT OF REDUCTION POTENTIAL AND REDUCTIVE ENZYME ACTIVITIES FOR BIOMASS FERMENTATION

(75) Inventors: Siddavattam Dayananda Siddavattam, Punjagutta Hyderabad (IN); Doddala Doddala Anitha Choudary, Punjagutta Hyderabad (IN); Karthikeyan Karthikeyan Venkatanarayanan, Punjagutta Hyderabad (IN)

(73) Assignee: Nagarjuna Fertilizers and Chemicals Limited, Nagarjuna Hills (IN)

( * ) Notice: Subject to any disclaimer, the term of this patent is extended or adjusted under 35 U.S.C. 154(b) by 609 days.

(21) Appl. No.: 12/918,534

(22) PCT Filed: Feb. 16, 2009

(86) PCT No.: PCT/IN2009/000105
§ 371 (c)(1),
(2), (4) Date: Mar. 7, 2011

(87) PCT Pub. No.: WO2009/113101
PCT Pub. Date: Sep. 17, 2009

(65) Prior Publication Data
US 2011/0152511 A1 Jun. 23, 2011

(30) Foreign Application Priority Data
Feb. 20, 2008 (IN) .............................. 422/CHE/2008

(51) Int. Cl.
*C12N 15/81* (2006.01)
*C12N 1/19* (2006.01)
*C07H 21/04* (2006.01)

(52) U.S. Cl.
USPC ...................... 435/471; 435/254.21; 536/23.1

(58) Field of Classification Search
None
See application file for complete search history.

(56) References Cited

U.S. PATENT DOCUMENTS

| 4,766,071 | A | 8/1988 | Simon et al. |
| 2,649,092 | A | 11/1993 | Skotheim et al. |
| 5,393,615 | A | 2/1995 | Corey et al. |
| 7,091,014 | B1 | 8/2006 | Aristidou et al. |
| 2008/0216181 | A1 | 9/2008 | Schulze et al. |

FOREIGN PATENT DOCUMENTS

| WO | WO 03/038067 | 5/2003 |
| WO | WO 2005/103239 | 11/2005 |

OTHER PUBLICATIONS

L. Baldoma et al., "Metabolism of L-Fucose and L-Rhamnose in *Escherichia coli*: Aerobic-Anaerobic Regulation of L-Lactaldehyde Dissimilation", Journal of Bacteriology, vol. 170, No. 1, pp. 416-421, Jan. 1988.
John W. Foster et al., "Regulation of NAD Metabolism in Salmonella Typhimurium: Molecular Sequence Analysis of the Bifunctional nadR Regulator and the nadA-pnuC Operon", Journal of Bacteriology, vol. 172, No. 8, pp. 4187-4196, Aug. 1990.
R.D. Gietz et al., "Transformation of Yeast by Lithium Acetate/Single-Stranded Carrier DNA/Polyethylene Glycol Method", Meth. Enzymol. vol. 350, pp. 87-96 (2004).
Mark R. De Graef et al., "The Steady-State Internal redox State (NADH/NAD) Reflects the External Redox State and is Correlated with Catabolic Adaptation in *Eseherichia coli*", Journal of Bacteriology, vol. 181, No. 8, pp. 2351-2357, Apr. 1999.
Michael R. Leonardo et al., "Role of NAD in Regulating the adhE Gene of *Escherichia coli*", Journal of Bacteriology, vol. 178, No. 20, pp. 6013-6018, Oct. 1996.
Felix Lopez De Felipe et al., "Cofactor Engineering: A Novel Approach to Metabolic Engineering in *Lactococcus lactis* by Controlled Experssion of NADH Oxidase", Journal of Bacteriology, vol. 180, No. 15, pp. 3804-3808, Aug. 1998.
Oscar Maestre et al., "Effects of ADH2 Overexpression in *Saccharomyces bayanus* During Alcohol Fermentation", Applied and Environmental Microbiology, vol. 74, No. 3, pp. 702-707, Feb. 2008.
S. Michnik et al., "Modulation of Glycerol and Ethanol Yields During Alcoholic Fermentation in *Saccharomyces cerevisiae* Strains Overexpressed or Disrupted for GPDI Encoding Glycerol 3—Phosphate Dehydrogenase", Yeast, vol. 13, pp. 783-793, Jul. 1997.
Gail Lorenz Miller, "U of Dinitrosalicylic Acid Reagent for Determination of Reducing Sugars", Analytical Chemistry, vol. 31, No. 3, pp. 426-428, Mar. 1959.
Elke Nevoigt et al., "Reduced Pyruvate Decarboxylase and Increased Glycerol-3-phosphate Dehydrogenase [NAD+] Levels Enhance Glycerol Production in *Saccharomyces cerevisiae*", Yeast, vol. 12, pp. 1331-1337, Oct. 1996.
T.L. Nissen et al., "Optimization of Ethanol Production in *Saccharomyces cerevisiae* by Metabolic Engineering of the Ammonium Assimilation", Metabol. Engg., vol. 2; pp. 69-77 (2000).
Darin B. Ostrander et al., "Effect of CTP Synthase Regulation by CTP on Phospholipids Synthesis in *Saccharomyces cerevisiae*", The Journal of Biological Chemistry, vol. 273, No. 30, pp. 18992-19001, Jul. 24, 1998.

(Continued)

*Primary Examiner* — Nancy T Vogel
(74) *Attorney, Agent, or Firm* — DLA Piper LLP US

(57) ABSTRACT

The present invention describes the genetic engineering of production microorganisms used in biotechnology to improve their properties so that they produce industrially useful products more efficiently from fermentable sugars derived from biomass. The engineered microorganisms endowed with functional coupling of oxidation and reduction of substrates by dehydrogenases requiring pyridine nucleotides (NAD/NADH) result in simultaneous enhancement of reduction potential enzyme activity involving the transfer of electrons. In particular, this invention relates to the construction of an excisable gene expression cassette for expression of two different dehydrogenases leading to enhanced production of ethanol.

9 Claims, 5 Drawing Sheets

(56) References Cited

OTHER PUBLICATIONS

F. Remize et al., "Glycerol Overproduction by Engineered *Saccharomyces cerevisiae* Wine Yeast Strains Leads to Substantial Changes in By-Product Formation and to a Stimulation of Fermentation Rate in Stationary Phase", Applied and Environmental Microbiology, vol. 65, No. 1, pp. 143-149, Jan. 1999.

George G. Roberts et al., "Transcriptome Profiling of *Saccharomyces cerevisiae* During a Transition from Fermentative to Glycerol-Based Respiratory Growth Reveals Extensive Metabolic and Structural Remodeling", Mol. Gen. Genomics, vol. 276, pp. 170-186, Jun. 2, 2006.

Mark D. Rose, "Isolation of Genes by Complementation in Yeast", Meth. Enzymol, vol. 152, pp. 481-504 (1987).

Ailen M. Sanchez et al., "Effect of Different Levels of NADH Availability on Metabolic Fluxes of *E. coli* Chemostat Cultures in Defined Medium", Journal of Biotechnology, vol. 117, pp. 395-405 (2005).

P.S. Sastry et al., "Apoptosis and the Nervous System", Journal of Neurochemistry, vol. 74, No. 1, pp. 1-20 (2000).

D. W. Templeton, "Determination of Ethanol Concentration in Biomass to Ethanol Fermentation Supernatants by Gas Chromatography", NREL Laboratory Analytical Protocol # LAP-011, May 5, 1994 (11 pages).

Hadi Valadi et al., "NADH-reductive stress in *Saccharomyces cerevisiae* induces the expression of the minor isoform of glyceraldehyde-3-phosphate dehydrogenase (TDH1)", Current Genetics vol. 45, No. 2, pp. 90-95, Feb. (2004).

Bert L. Vallee et al., "A Component of Yeast Alcohol Dehydrogenase", Proceeding of the National Academy of Sciences, vol. 41, No. 6, pp. 327-337, Jun. 15, 1955.

P. Van Hoek et al., "Regulation of Fermentative Capacity and Levels of Glycolytic Enzymes in Chemostat Cultures of *Saccharomyces cerevisiae*", Enzyme and Microbial Technology, vol. 26, pp. 724-736, Jun. 2000.

V. Worthington, "Glyceraldehyde 3-phosphate Dehydrogenase", Worthington Enzyme Manual, 1993 Edition, Wothington Biochemical Corporation, New Jersey, USA, pp. 201-206 (1993).

Wilma Martinez Arias et al., "Mechanism of NADH Transfer Between Alcohol Dehydrogenase and Glyceraldehyde-3-Phosphate Dehydrogenase", Eur. J. Biochem., vol. 250, pp. 158-162 (1997).

International Search Report Issued in International Application No. PCT/IN2009/000105, dated Sep. 1, 2009.

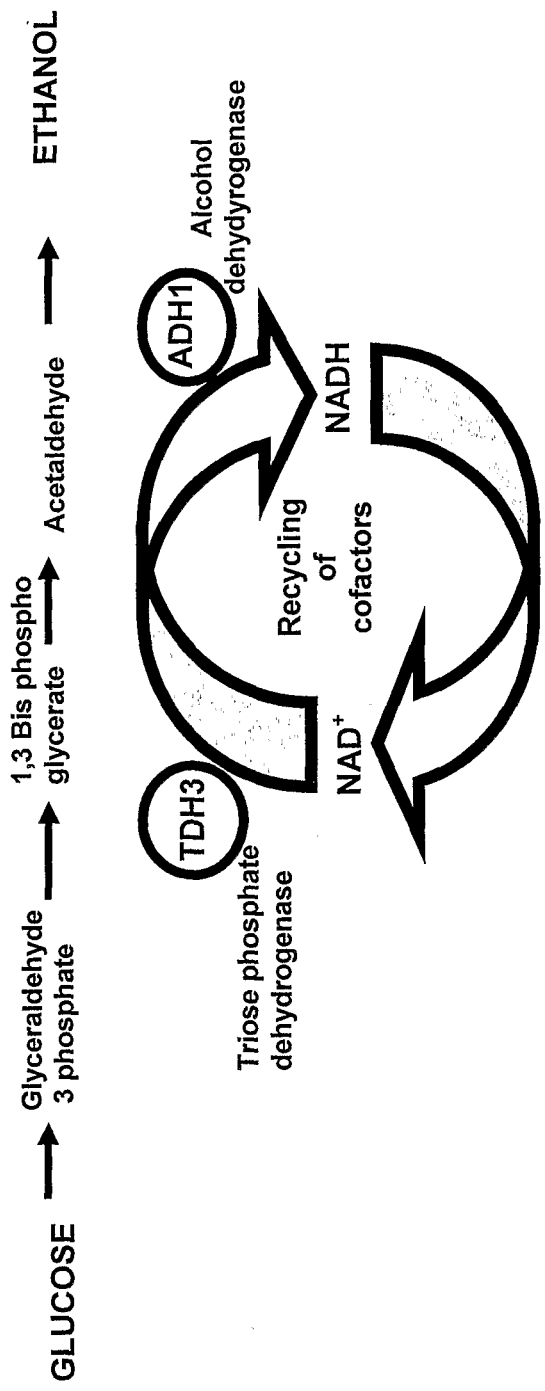
Fig1: Recycling of reduction potential

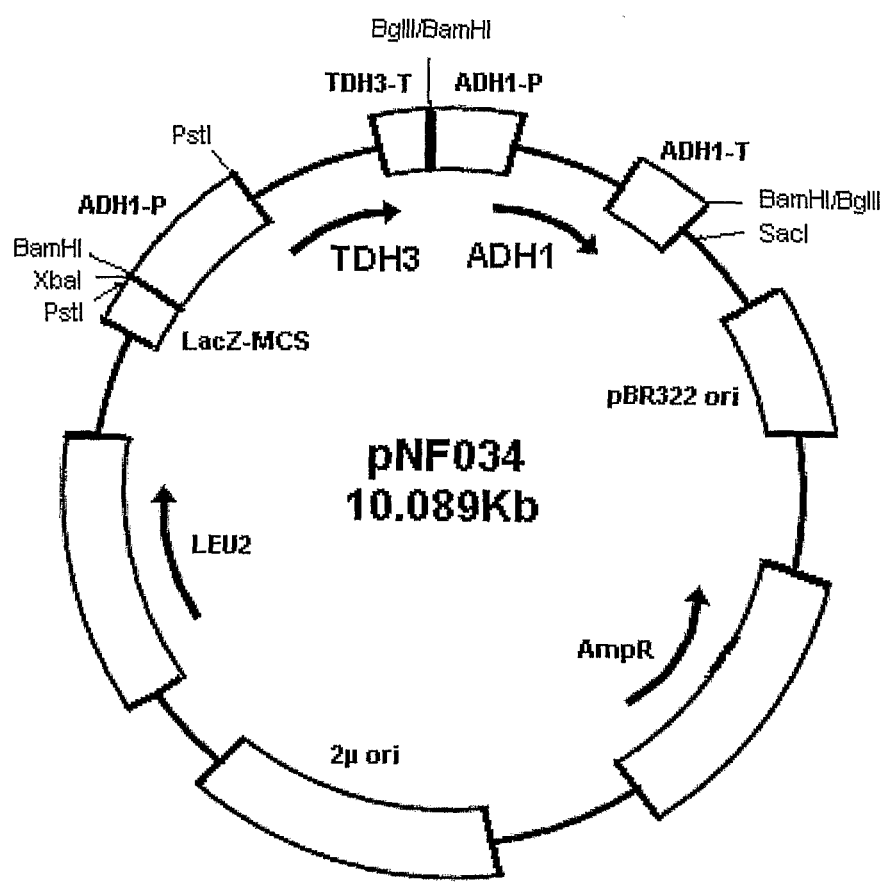
Fig 2: Genetic map of plasmid pNF034

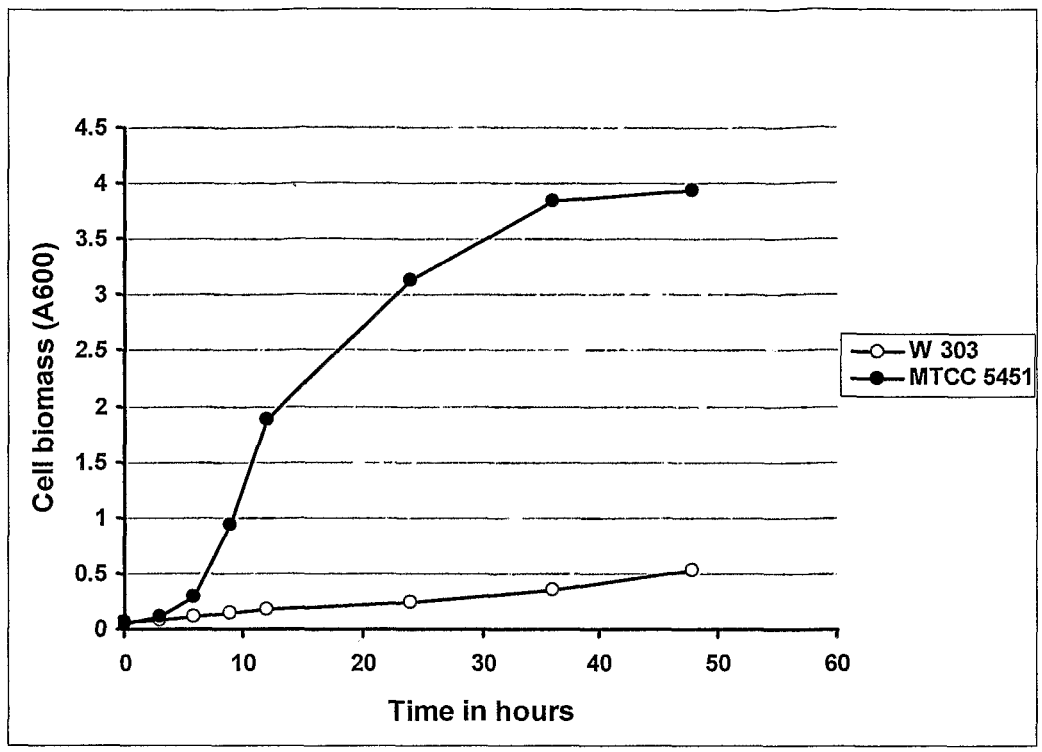
Fig 3: Growth pattern of W 303 and MTCC 5451
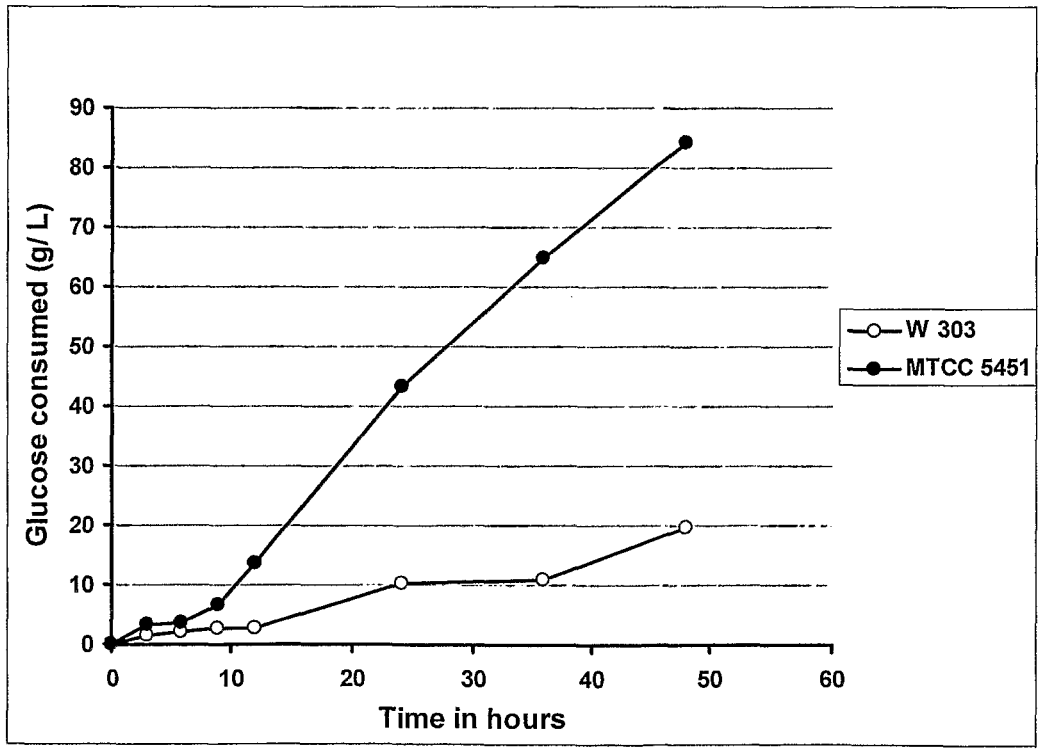
Fig 4: Glucose consumption profiles of W 303 and MTCC 5451

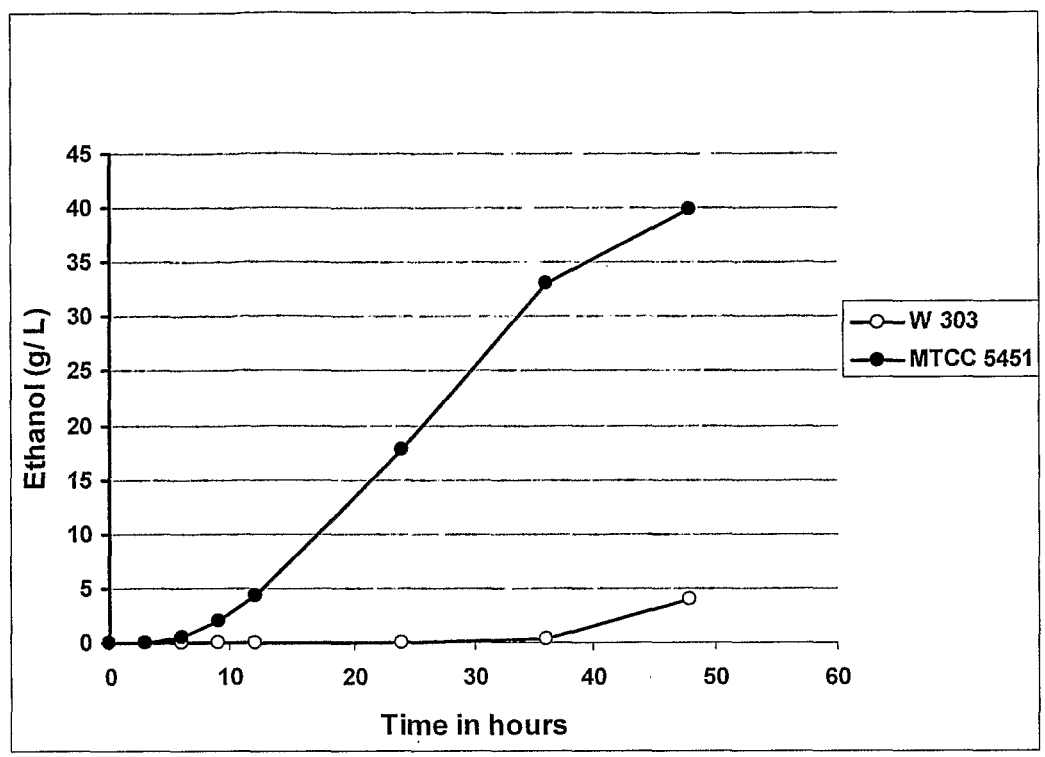
Fig 5: Total ethanol production by W 303 and MTCC 5451
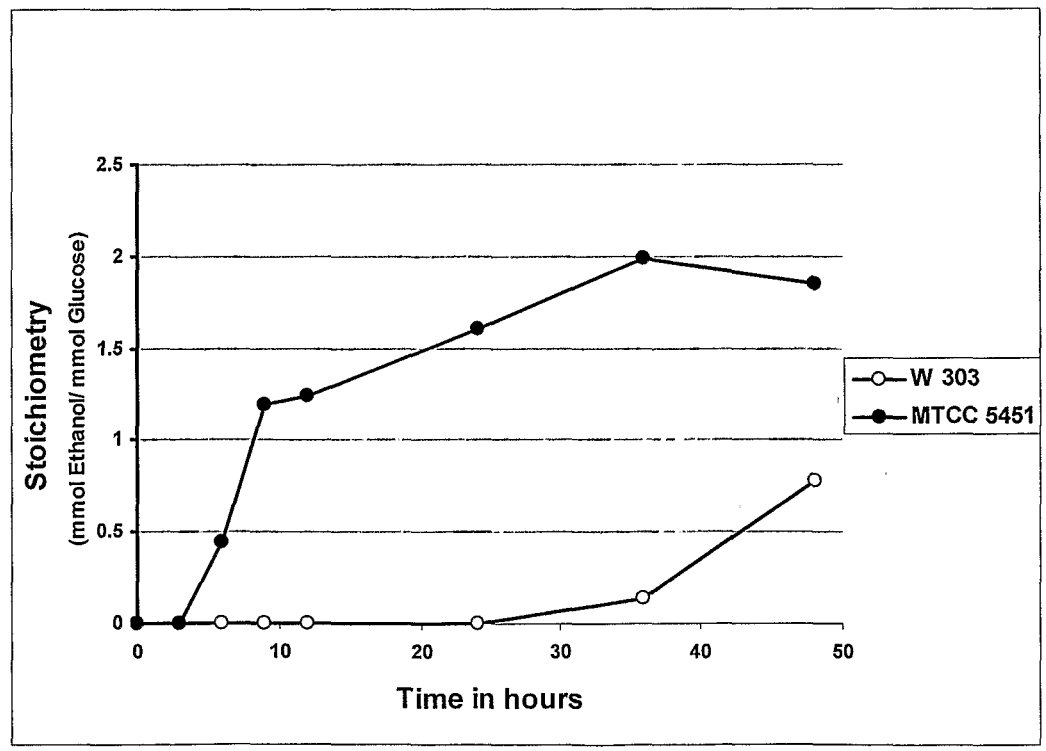
Fig 6: Stoichiometric relationship between ethanol production and glucose consumption by W 303 and MTCC 5451

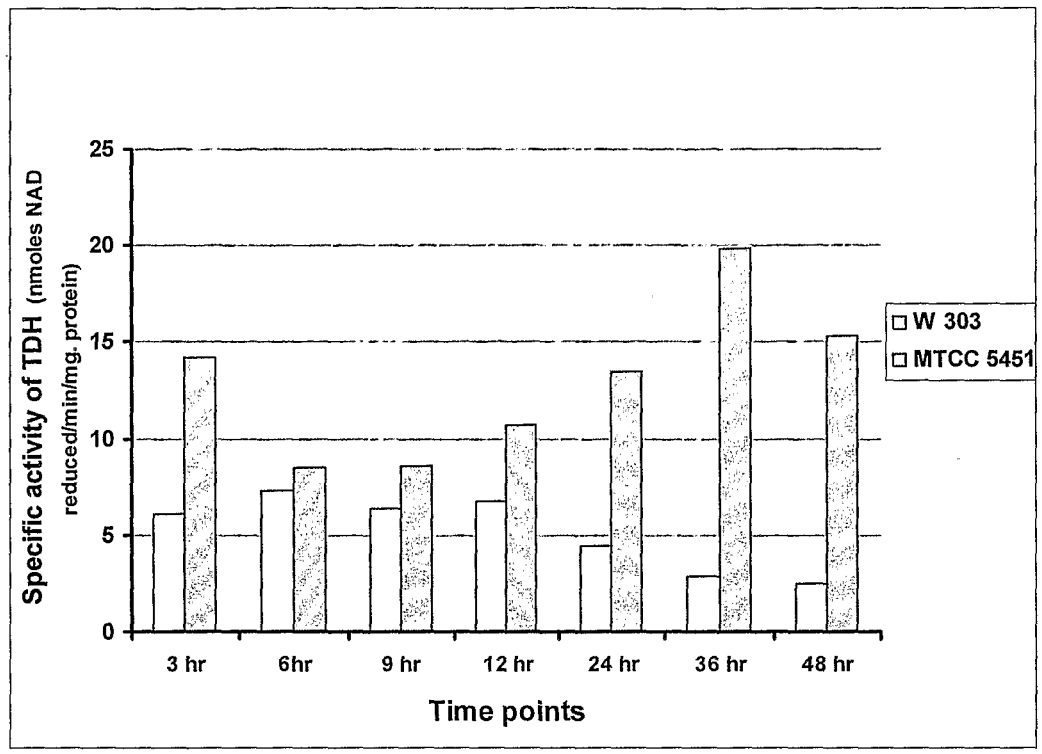
Fig 7: Comparative profiles of TDH activity in W 303 and MTCC 5451
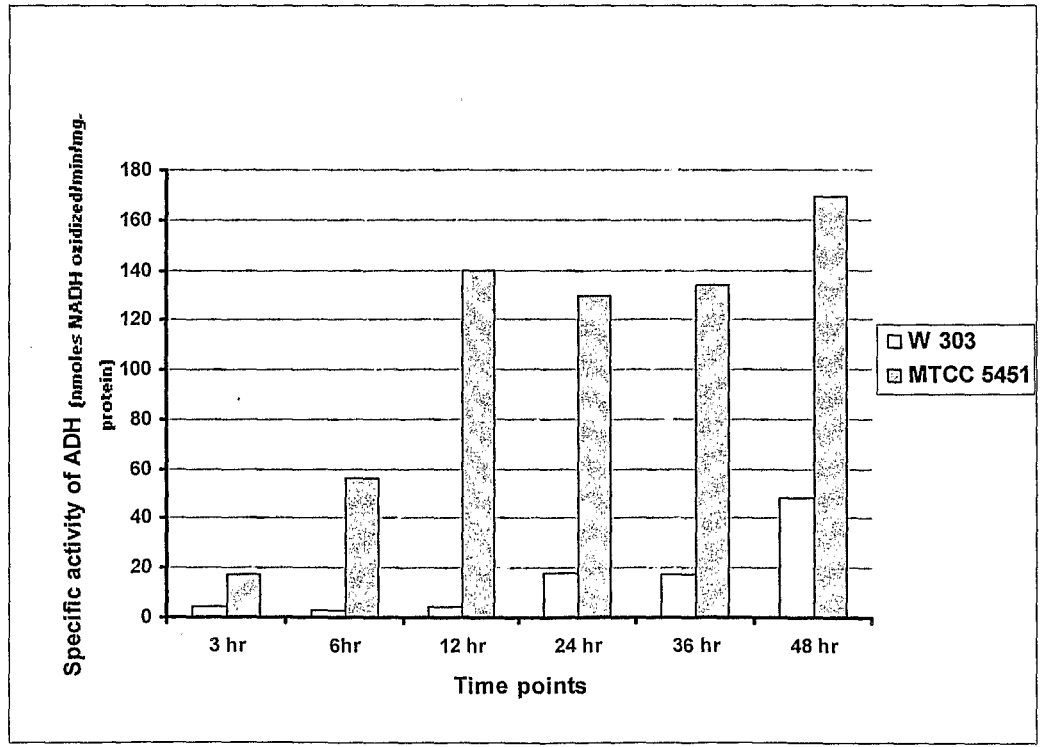
Fig 8: Comparative profiles of ADH activity in W 303 and MTCC 5451

GENETICALLY TRANSFORMED MICROORGANISMS WITH SIMULTANEOUS ENHANCEMENT OF REDUCTION POTENTIAL AND REDUCTIVE ENZYME ACTIVITIES FOR BIOMASS FERMENTATION

FIELD OF INVENTION

The present invention relates to genetic engineering of microorganisms used in biotechnology to improve their properties so that they produce industrially useful products from sugars derived from biomass more efficiently. In particular, this invention relates to the construction of an excisable gene expression cassette and promoter sequences for the expression of two different dehydrogenases leading to enhanced production of metabolites such as ethanol.

BACKGROUND OF THE INVENTION

The ability of microorganisms to produce greater yields of commercially important products at efficient rates can be achieved through metabolic engineering approaches involving amplification, addition or deletion of key enzymes catalyzing relevant metabolic reactions in the concerned metabolic pathways. Redox reactions, catalyzed by enzymes generally referred to as oxidoreductases, in several metabolic pathways are involved in the production of many industrially important compounds. Considering that maintenance of cellular redox balance is the basic requirement for cellular growth and metabolism, as well as for the efficiency with which microorganisms produce commercially important metabolites, manipulation of genes responsible for the maintenance of optimal redox balance provides an additional tool in metabolic engineering of microorganisms. Among various cofactors, pyridine nucleotides namely nicotinamide adenine dinucleotide (NAD) and nicotinamide adenine dinucleotide phosphate (NADP) serve as universal, soluble electron carriers and function as cofactors for several dehydrogenase enzymes. NAD—involved in catabolic pathways and NADP—involved in anabolic pathways undergo reversible reduction concomitant with oxidation (dehydrogenation) of the substrate molecule to function as cofactors for several dehydrogenases. In particular, NAD—in its oxidized ($NAD^+$) and reduced ($NADH+H^+$) forms—functions as the cofactor in over 300 redox reactions and serves not only as an electron acceptor in catabolism but also provides the cell with reducing power in energy conserving redox reactions that occur in aerobic and anaerobic respiration (Foster et al., 1990). A balance in the rates of oxidation and reduction of these nucleotides is a pre-requisite for continuation of catabolism and anabolism since their turnover is higher than their cellular concentrations.

People in the knowledge of prior art are aware of the exergonic pathways which are involved in glucose catabolism under anaerobic conditions results in energy generation—in the form of adenosine triphosphate (ATP)—that is tightly coupled with the generation of $NADH+H^+$ as shown below:

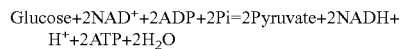

$$\text{Glucose}+2NAD^{+}+2ADP+2Pi=2\text{Pyruvate}+2NADH+H^{+}+2ATP+2H_{2}O$$

Of the two energy conserving reactions of glycolysis, which eventually lead to the formation of ATP, the oxidation of glyceraldehyde 3-phosphate to 1,3-bisphophoglycerate is important since it is concomitant with the reduction of $NAD^+$. Subsequent conversion of pyruvate, a key intermediate in catabolism and the common product of all free energy sources, to either acetaldehyde (by decarboxylation) and further into ethanol or to lactate (by reduction) under anaerobic conditions or to acetyl Co A (by oxidative decarboxylation) under aerobic conditions is largely determined by cellular oxidative status as well as the reactions wherein oxidation of $NADH+H^+$ is achieved to regenerate $NAD^+$. In the absence of regenerating $NAD^+$, the cells would be depleted of electron acceptor required for oxidation of glyceraldehyde 3-phosphate and energy yielding reactions of glycolysis would halt.

In addition to the above role as cofactors, pyridine nucleotide cofactors also regulate gene expression. Thus, limiting NAD synthesis decreased the expression of adhE and increasing NADH concentrations leads to the induction of adhE gene (Leonardo, 1996).

In continuation of the above knowledge accrued from cellular studies, efforts made to engineer the cellular redox potentials by varying relative turnover and yield of $NAD^+$ and $NADH+H^+$ have resulted in significant improvements towards modulating commercial production of metabolites by microorganisms. Most of the currently available strategies of cofactor engineering target (a) the dehydrogenases involved in oxidation and reduction of NAD or (b) enhancing the relative contents of these pyridine nucleotides.

Metabolic engineering approaches made towards amplification or interruption or addition of metabolic pathways has yielded significant results. Importantly, our knowledge of the physiological roles of glycerol in the oxidation of surplus NADH and ethanol in ATP formation has been exquisitely utilized in metabolic engineering.

Notable examples of cofactor engineering by modulating $NAD^+/NADH$ ratios towards specific production of targeted metabolites, among others, include:

i) Enhanced availability of $NADH+H^+$ can lead to overexpression of adhE gene (coding for alcohol dehydrogenase) in *Escherichia coli*, causing enhanced ethanol production under fermentative conditions (Leonardo et al, 1996).

ii) Shift between oxidation or reduction of L-lactaldehyde could be regulated by inhibition of pyruvate dehydrogenase complex by high NADH/NAD ratios (Graef et al., 1999; Baldoma and Aguilar, 1988).

iii) Overexpression of the NADH-dependent glycerol 3-phosphate dehydrogenase (GPD) resulted in a shift of carbon flux towards glycerol production, as well as that of succinate and acetate, at the expense of ethanol production (Remize et al, 1999).

iv) Modulation of glycerol and ethanol yields could also be obtained upon over expressing or disrupting the GPD coding for glycerol 3-phosphate dehydrogenase in *Saccharomyces cerevisiae* (Nevoigt, 1998).

v) While disrupting GPD 1 resulted in decreased glycerol production and enhanced ethanol formation, overexpression of the gene resulted in significant increase in acetaldehyde formation as well as marked accumulation of pyruvate, acetate, acetoin, 2,3 butanediol and succinate. These alterations could be attained from competitive regeneration of NADH via glycerol 3-phosphate dehydrogenase (Michnik et al, 1998).

vi) Nissen et al (2000) substituted the normal NADPH consuming synthesis of glutamate from ammonium and 2-oxoglutarate in *Saccharomyces cerevisiae* vii) with a new pathway marked by consumption of NADH and ATP. The resultant yeast strain produced higher ethanol and lower glycerol yields as compared to the parent wild type strain under anaerobic fermentative conditions.

Metabolic shift from homolactic to mixed acid fermentation was achieved upon cloning the nox2 gene coding for NADH oxidase from *Streptococcus mutans* into *Lactobacter lactis*. Under aerobic conditions, the observed shift in transformants was modulated by the level of NADH oxidation resulting in lowered NADH/NAD+ ratios (Lopez De Felipe et al, 1998).

Efforts were also made to regenerate the used cofactors, such as NAD+ and NADH, considering the critical importance of in cofactor-dependent industrial production. These include:

i) In vivo regeneration of NADH employing cellular lysates of *Clostridium kluyveri* in combination with an aldehyde as an oxidizing agent (U.S. Pat. No. 4,766,071)

ii) Using an electrode to mediate electrochemical regeneration of NADH (U.S. Pat. No. 5,393,615)

iii) Employing coated polymers containing mediators that are covalently linked to the polymeric backbone (U.S. Pat. No. 5,264,092)

In addition to the above, specific strategies for increasing intracellular production of NADH have also been examined in *Escherichia coli*. These include (a) feeding carbohydrates with different oxidation states, (b) eliminating pathways using NADH (such as lactate dehydrogenase and alcohol dehydrogenase) that compete for NADH, (c) over expressing NAD+ dependent formate dehydrogenase to regenerate NADH, (d) over expressing nicotinic acid phosphoribosyl transferase that converts exogenously added nicotinic acid to nicotinamide mononucleotide. Of these approaches, varying NADH availability by combining external and genetic means i.e., feeding different carbon sources with different oxidation states to *Escherichia coli* strains over expressing nicotinic acid phosphoribosyl transferase resulted in enhancing intracellular NADH contents to certain extent. Heterologous expression of *Candida boidinii* NAD+-dependent formate dehydrogenase in *E. coli* enhanced the maximal yield of NADH, arising from glucose or sorbitol, from the theoretical maximum of 2 moles to 4 and 4.6 moles per mole of the respective substrate. *E. coli* strains transformed with heterologous formate dehydrogenase and using sorbitol as the carbon source demonstrated increased ethanol production reflecting on enhanced availability of NADH (Sanchez et al, 2005)

Inventors and scientists in the knowledge of prior art would appreciate that the common motif in the above attempts is to alter NAD/NADH ratios that influence cellular redox balance by targeting one of the several dehydrogenases involved in glycolysis or its related pathways. Thus, manipulation of genes coding for alcohol dehydrogenase or pyruvate dehydrogenase or glycerol 3-phosphate dehydrogenase or formate dehydrogenase was resorted to channel metabolic fluxes towards the formation of microbial metabolites such as ethanol or acetic acid or pyruvate or acetoin or butanediol or succinate. However, all of these dehydrogenases are involved in reducing substrates utilizing reduced NAD (NADH) as the cofactor. Only limited efforts were made to manipulate or over express dehydrogenases involved in the production of NADH.

Glyceraldehyde 3-phosphate dehydrogenase catalyzes the following reaction involving the oxidation of glyceraldehyde 3-phosphate to 1,3-bisphosphoglycerate—the first step in the payoff phase of glycolysis.

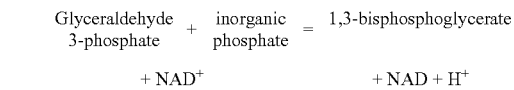

The acceptor for hydrogen in the reaction is NAD+ involving enzymatic transfer of a hydride ion (:H−) from the aldehyde group of glyceraldehyde 3-phosphate to nicotinamide ring of NAD to yield reduced cofactor NADH; the other hydrogen atom of the substrate appears as H+ in solution. The high amount of standard free energy of the reaction ($\Delta G^{0\prime}$=−49.3 KJ/mol) is utilized for the formation of ATP in the subsequent reaction wherein 1,3-bisphophoglycerate is converted to 3-phosphoglycerate. Glyceraldehyde 3-phosphate dehydrogenase is the only source of NADH in glycolysis, which is the primary catabolic pathway in the utilization of fermentable sugars and involved in glycolysis and gluconeogenesis by microorganisms. Glyceraldehyde 3-phosphate dehydrogenase is a tetramer distributed in the cytoplasm and cell walls of fermentative producers such as *Saccharomyces*. In *Saccharomyces* three unlinked genes (~1 kbp) entitled TDH1, TDH2, and TDH3 encode related but not identical, catalytically active homoteramers with different specific activities involved in metabolic and structural remodeling (Roberts et al. 2006). While TDH3 protein accounts for 50-60% of total activity, proteins coded by TDH1 and TDH2 respectively account for 10-15% and 25-30% of the total activity.

Among the genes coding for TDH enzymes, TDH1 and TDH2 are located on chromosome X and TDH3 is located on chromosome VII. None of these structural genes is individually essential for cell viability even though the presence of a functional TDH2 or TDH3 gene is mandatory for cell viability. However, it is reported that TDH1 interacts with GTS1 involved in ultradian oscillations of glycolysis and improves anaerobic growth of yeast cultures devoid of glycerol phosphate dehydrogenase (GPD2) gene (Valadi et al. 2004). Despite such extensive information available on the physiological and genetic role of TDH genes, the innate ability of TDH genes towards cofactor engineering has not been exploited towards commercial metabolite production by producer microorganisms. A need therefore still exists for the generation of stable genomic inserts or gene cassettes that encode the necessary enzymes for sugar catabolism for high product formation close to maximum theoretical yield.

Treading on a new line of thought, we made efforts to combine the events related to production and utilization of NADH in order to engineer cofactor requirements related to microbial metabolite production. These experiments resulted in the present invention that describes novel DNA constructs and method for creating a physiological situation wherein greater reduction potential is continuously produced and utilized in a cyclic manner upon over expression of two dehydrogenases involved in production and utilization of NADH. Such an approach would increase specific productivity of industrially important products from sugars by industrial microorganisms. The novelty of the present innovation is also related to the fact that we have engineered two different dehydrogenase enzymes, wherein one is involved in the production of NADH and the other one is involved in the utilization of NADH. This approach is distinctly different from the above-cited approaches wherein only one dehydrogenase that either produces or utilizes NADH has been targeted and used to enhance microbial metabolite production. More importantly, such an approach results in cyclic production and utilization of NADH to augment microbial metabolite production. Because both the enzymes are components of a single metabolic pathway viz., glycolysis, and since both the dehydrogenases are integral components contributing to product formation, such an approach would enhance the channeling of substrate towards product formation.

SUMMARY OF THE INVENTION

The objective of this invention is to describe a method to generate a novel DNA construct or gene expression cassette comprising of triosephosphate dehydrogenase (TDH3) gene driven by alcohol dehydrogenase (ADH1) promoter followed by alcohol dehydrogenase (ADH1) gene driven by ADH1 promoter. This gene expression cassette, either as a monomer or as one or more copies of multimers, has the capability to enhance generation and concomitant utilization of reduction potential to increase fermentative production of industrially important products. The functional coupling of oxidation and reduction of pyridine nucleotide linked dehydrogenases involved in glycolysis facilitates cyclic transfer of reduction potential between the two dehydrogenases. The other aspect of the invention describes a method for transforming and selecting recombinant microorganisms such as a bacterium or yeast possessing at least one recombinant DNA molecule encoding or otherwise causing the expression of at least one of the aforementioned two dehydrogenases. Increased availability of reduction potential by providing greater amounts of reduced nicotinamide adenine dinucleotide (NADH+H$^+$) contributes to increased rate of product formation and the resulting recombinant microorganism possesses the ability for efficiently producing fermentation products from the renewable carbon source such as biomass. Preferable microorganisms for purposes of this invention include yeasts, filamentous fungi and bacteria. Preferable yeasts are members of the *Saccharomyces* group and especially strains of *Saccharomyces* species. Thus, this novel invention describes genetically engineered industrial microorganisms, gene expression cassettes and the processes for the fermentation of biomass carbohydrates to useful industrial products by the modified microorganisms. Thus the main advantage of the present invention is that it results in cyclic production and utilization of NADH in the modified organism which results in higher yields of fermentation products, due to the increased amount of NADH available for the biotransformation.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and form a part of this specification, illustrate one or more embodiments of the present disclosure and, together with the detailed description, serve to explain the principles and implementations of the disclosure.

FIG. 1: Schematic representation of glycolytic pathway illustrating recycling of reduction potential involved in the production of ethanol from glucose.

FIG. 2: Genetic map of pNF034 with the excisable gene cassette and restriction sites. Multimerization of the gene cassette is possible by cloning the cassette taken as BamHI-BglII fragment in the unique BamHI site.

FIG. 3: Glucose fermentations by *Saccharomyces cerevisiae* recombinant strain expressing the excisable gene cassette (tNF006; solid symbols) and its parent strain (W303; open symbols); comparison of growth patterns.

FIG. 4: Glucose fermentations by *Saccharomyces cerevisiae* recombinant strain expressing the excisable gene cassette (tNF006; solid symbols) and its parent strain (W303; open symbols); comparison of glucose consumption.

FIG. 5: Glucose fermentations by *Saccharomyces cerevisiae* recombinant strain expressing the excisable gene cassette (tNF006; solid symbols) and its parent strain (W303; open symbols); comparison of ethanol production.

FIG. 6: Glucose fermentations by *Saccharomyces cerevisiae* recombinant strain expressing the excisable gene cassette (tNF006; solid symbols) and its parent strain (W303; open symbols); comparison of rate of ethanol production.

FIG. 7: Glucose fermentations by *Saccharomyces cerevisiae* recombinant strain expressing the excisable gene cassette (tNF006; solid symbols) and its parent strain (W303; open symbols); comparison of glyceraldehyde 3-phosphate dehydrogenase activities FIG. 8: Glucose fermentations by *Saccharomyces cerevisiae* recombinant strain expressing the excisable gene cassette (tNF006; solid symbols) and its parent strain (W303; open symbols); comparison of alcohol dehydrogenase activities.

DETAILED DESCRIPTION OF INVENTION

The present disclosure refers to a recombinant microorganism engineered to cyclic production and utilization of NADH in the modified organism which results in higher yields of fermentation products, due to the increased amount of NADH available for the biotransformation.

The term "Gene" as used in this specification refers to a segment of deoxyribonucleotides (DNA) possessing the information required for synthesis of a functional biological product such as a protein or ribonucleic acid (RNA).

The term "Genetic engineering" is used to indicate various methods involved in gene manipulation including isolation, joining, introducing of gene(s) as well as methods to isolate select organisms containing the manipulated gene(s).

As specified herein, the term "DNA construct" refers to a sequence of deoxyribonucleotides including deoxyribonucleotides obtained from one or more sources.

The term "Gene Expression" refers to efficient transcription and translation of genetic information contained in concerned genes.

As used herein, an "excisable gene cassette" refers to a construct containing genes in a vector leading to simultaneous enhancement of reduction potential and reductive enzyme activities.

As used herein, the term "Coordinate expression" signifies simultaneous expression of genes with regard to the cellular location and time of appearance of products coded by concerned genes.

The term "Promoter" refers to deoxyribonucleotide sequences that are present upstream (in the 5' to 3' direction) to the deoxyribonucleotide sequences constituting a gene. The term "Monomer" refers to a single unit of the gene expression cassette (defined above) and a "multimer" containing more than one unit of the gene expression cassette.

The term "Redox Potential" refers to the reduction/oxidation potential of a compound measured under standard biological conditions and at pH 7.0. The term is also used herein as a measure of oxidizing and reducing strengths of electron carriers, more specifically related to the standard redox potential of NAD and NADH (E°'=−0.32 Volts) and the enzymatic reactions which depend on NAD and NADH as cofactors for their activity. Accordingly, the terms "Generation" and "Utilization" of reduction potential refer to biological reactions involved in the formation and disappearance of reduced NAD (NADH).

As used herein, the term "Cyclic transfer" signifies reactions involving the functional coupling of oxidation and reduction reactions catalyzed by specific dehydrogenase enzymes.

The term "recombinant" cells or population of cells refers to cells or population of cells into which an exogenous nucleic acid sequence is introduced using a delivery vehicle such as a plasmid.

As used herein the term "cyclic transfer of reduction potential" refers to the engineered, recombinant system that facilitates continuous generation and utilization of reduction potential.

The term "Microorganism" mentioned herein refers to one or more forms/species of bacteria or yeast.

The term "Microaerophilic condition" refers to an environment with low oxygen conditions wherein a microorganism can propagate.

Glycolysis (Greek: glykys=sweet; lysis=splitting) is the ubiquitous, central catabolic pathway involving the anaerobic degradation of glucose to yield two molecules of pyruvate through a series of enzyme-catalyzed reactions. The glycolytic pathway is amphibolic because it provides the cell with not only biological energy in the form of the high-energy compound, adenosine triphosphate (ATP) but also yields C 3 precursors required for the biosynthesis of biomolecules such as amino acids, fatty acids and cholesterol. In addition to the above, this anaerobic metabolic pathway is also the source for generation of the reduced pyridine nucleotide—NADH. Glyceraldehyde 3-phosphate dehydrogenase that catalyzes the concerned reaction of converting glyceraldehyde 3-phosphate to 1,3-bisphosphoglycerate is a key enzyme in glycolysis since it is the only enzyme contributing to NADH in glycolytic conversion of glucose to pyruvate. Besides its biocatalytic role of this highly conserved protein contributes to several other important cellular functions such as microtubule bundling facilitation, protein kinase modulation and activation of neuronal transcription (Sastry and Rao, 2000). In the anaerobic fermentative pathway of glucose breakdown, glyceraldehyde 3-phosphate dehydrogenase is the only enzyme responsible for oxidation potential involved in the conversion of an aldehyde to an acid with concomitant reduction of oxidized NAD to reduced NAD (NADH). In subsequent reactions of glycolysis, pyruvate (a 3-carbon compound) is formed. Further conversion of pyruvate to various metabolites such as ethanol or lactate involves the oxidation of NADH generated earlier by glyceraldehyde 3-phosphate dehydrogenase, culminating in the regeneration of $NAD^+$ so that the glycolytic pathway can be continuously operative (FIG. 1).

As an example of engineering and recycling the reduction potential that contributes to enhanced microbial productivity, we have manipulated the native genetic architecture of Saccharomyces cerevisiae for improving its fermentative abilities of ethanol production. Towards this, we have engineered the candidate genes (TDH3 and ADH1), placed them under the control of a common ADH1 promoter, and thus generated an excisable gene cassette, which can be obtained as a restriction fragment. This cassette can be inserted into any vector, plasmid, or organism as a single unit or in multiple units to generate tandem repeats facilitating enhanced gene dosage. Such enhanced gene dosage will increase the gene-directed synthesis of dehydrogenases resulting in enhanced availability of reduced cofactor (NADH) catalyzed by TDH3 as well as the regeneration of oxidized $NAD^+$ caused by ADH1 enzyme expression in higher quantities. Such a rapid turnover of redox potential, as represented by increased oxidation and reduction of NAD in a cyclic fashion, would accelerate the rate/yield of microbial metabolites such as ethanol by industrial microorganisms such as yeast or bacteria that ferment carbohydrates derived from biomass.

One embodiment of the present invention describes the method to construct the gene cassette encoding glyceraldehyde 3-phosphate dehydrogenase followed by alcohol dehydrogenase of Saccharomyces cerevisiae, both driven independently by ADH1 promoter. Towards this, the ADH1 promoter was obtained by digesting pDO105, the yeast shuttle vector containing the ADH1 promoter, with BamHI and PstI as reported earlier by Ostrander (1998). TDH3 gene coding for glyceraldehyde 3-phosphate dehydrogenase and ADH1 gene coding for alcohol dehydrogenase were amplified from total genomic DNA of a laboratory S. cerevisiae strain (ATCC collocation No. BY4742). The promoter and the genes were serially introduced into a cloning vector (pBSKS obtained from ATCC) to achieve the construction of the recombinant pBSKS plasmid containing the gene cassette. The gene cassette was excised from the recombinant pBSKS vector upon digestion using BamHI and BglII for introducing it into the yeast shuttle vector (YEp351). The resultant recombinant YEp351 plasmid was designated as pNF034.

In another embodiment of the present invention, a strain of S. cerevisiae (W303 from ATCC) was transformed with pNF034. The method of Gietz and Woods (2004) was adapted with minor modifications to obtain transformants. The procedure involved culturing yeast cells to a density of $\sim 1.2 \times 10^7$ per ml in a medium made of 2% yeast extract, 4% peptone and 4% dextrose containing 10 mg % adenine hemisulphate. The cells were subjected to heat shock in the transformation mix containing 0.1 M lithium acetate, 100 µg single stranded DNA and 33.3% polyethylene glycol at 42° C. for 180 minutes. The cells were washed with sterile water and plated on synthetic medium devoid of leucine in order to select transformants (Rose 1987a). Transformants were selected by leucine auxotrophic mutation and wild type gene complementation. Transformants were verified by isolating the recombinant pNF034 plasmid and digestion with BamHI. Confirmed transformants were designated as tNF006.

In yet another embodiment of the invention, the ability of yeast transformants (tNF006) to produce ethanol was verified under fermentative conditions and compared with that of the parent W303 cells. The parent yeast strain was cultured in complete synthetic medium containing 0.67% yeast nitrogen base, 10% glucose and supplemented with amino acids, uracil and adenine hemisulphate as specified in the Gietz lab protocol available in the public domain. While culturing tNF006, leucine was excluded from the culture media to ascertain auxotrophic nature of the transformant Equal number of cells ($5 \times 10^6$ cells) were cultured in sealed bottles containing 500 ml of media as specified above at 28±2° C. for 48 hours. Aliquots (50 ml) were withdrawn at specified time periods and evaluated for growth, glucose consumption and alcohol production.

EXAMPLES

Example 1

Methods to Construct the Recombinant Plasmid pNF034

In order to obtain genetically transformed microorganisms endowed with simultaneous enhancement of reduction potential and reductive enzyme activities, the recombinant plasmid pNF034 was constructed. This plasmid, contains the gene cassette encoding glyceraldehyde 3-phosphate dehydrogenase followed by alcohol dehydrogenase of *Saccharomyces cerevisiae*, both driven independently by ADH1 promoter. The attached gene sequence depicts the alignment of amino acid sequence deduced from nucleotide sequence of the excisable gene cassette encoding glyceraldehyde 3-phosphate dehydrogenase followed by alcohol dehydrogenase of *Saccharomyces cerevisiae* both driven independently by ADH1 promoter. The nucleotide sequences 1-1516 denote ADH1 promoter; the nucleotide sequences 1517-1559 denote Kozak sequences upstream to TDH3 gene; the nucleotide sequences 1560-2558 denote the open reading frame (ORF) of TDH3 gene; the nucleotide sequences 2559-2815 denote terminator region for transcription of TDH3 gene; the nucleotide sequences 2816-3193 denote ADH1 promoter; the nucleotide sequences 3194-4240 denote opening reading frame of ADH1 gene; the nucleotide sequences 4241-4451 denote terminator region for transcription of ADH1 gene. The consensus promoter sequences of *S. cerevisiae* that facilitate transcription are at nucleotide sequences of 1343-1350 and at 3066-3072.

Part 1: Cloning the ADH1 Promoter into PBSKS Cloning Vector

As an initial step for construction of pNF034, sequences corresponding to ADH1 promoter (sequences numbering 1-1516) were obtained by digesting pDO105 plasmid with BamHI and PstI. The obtained fragment was ligated at the BamHI and PstI sites situated in the multiple cloning site under the control of lac promoter of the bacterial cloning vector pBSKS using T4 DNA ligase and transformed into *Escherichia coli* DH5α strain. The transformants obtained were selected upon blue-white selection using isopropyl thiogalactoside (IPTG) as the inducer and 5-bromo-4 chloro-3-indolyl-β-D-galactopyranoside (X-gal) as the chromogenic substrate. Restriction digestion of recombinant pBSKS containing the ADH1 promoter with BamHI and PstI to obtain the 1516 bp fragment as well as verifying the concerned nucleotide sequence confirmed the ADH1 promoter.

Part 2: Cloning the TDH3 Gene into Recombinant pBSKS Vector Containing ADH1 Promoter:

The ORF corresponding to glyceraldehyde 3-phosphate dehydrogenase in *Saccharomyces cerevisiae* (SGD No. YGR192C) was amplified from yeast chromosomal DNA by polymerase chain reaction (PCR). Primers complementary to the ends of the TDH3 gene (forward primer SEQ ID No. 1=5'-CACCAAGAACTTAGTTTCG-3'; reverse primer SEQ ID No. 2:=5'-CCCCAAAATTATTAAGAGCGCC-3') were used to amplify this gene from chromosomal DNA isolated from *S. cerevisiae* BY4742. The forward primer contained a restriction site for PstI at the 5' terminii and the reverse primer contained sites for digestion with Eco RI and BglII at the 5' terminii. PCR conditions were: hot start at 95° C. 5 min, 95° C. 1 min, 60° C. 1 min, 72° C. 1.5 min; 30 cycles, final extension at 72° C., 5 min. The PCR product representing TDH3 gene was digested with PstI and EcoRI and purified from 0.5% agarose gels. The TDH3 gene was ligated downstream to ADH1 promoter at PstI and EcoRI sites of recombinant pBSKS vector as obtained through Example 1, Part I described above.

Part 3: Cloning the ADH1 Gene into Recombinant pBSKS Vector Containing ADH1 Promoter and TDH3 Gene:

The ADH1 gene encoding the ORF of alcohol dehydrogenase, along with its promoter and terminator sequences (SGD No. YOL086C) was amplified from chromosomal DNA of *S. cerevisiae* by PCR. Primers complementary to the ends of the ADH1 gene (forward primer SEQ ID No. 3=5'-CTC-CCCCGTTGTTGTCTCACC-3'; reverse primer SEQ ID No. 4=5'-GGCATTTGCTCGGCATG CCGG-3') to amplify this gene from chromosomal DNA isolated from *S. cerevisiae* BY4742. The forward primer contained a restriction site for BamHI at the 5' terminii and the reverse primer contained sites for digestion with BglII at the 5' terminii. PCR conditions were: hot start at 95° C. 5 min, 95° C. 1 min, 69.2/66.8° C. 1 min, 72° C. 1.5 min; 30 cycles, final extension at 72° C., 5 min. This PCR product was ligated at the BglII site of the recombinant plasmid obtained through Example 1, Part 2 described above.

The gene cassette obtained as above and encoding glyceraldehyde 3-phosphate dehydrogenase followed by alcohol dehydrogenase of *Saccharomyces cerevisiae*, both driven independently by ADH1 promoter (depicted in FIG. 2) resident in the resultant recombinant pBSKS vector, was obtained by digestion of recombinant plasmid obtained through Example 1, Part 3 with BamHI and BglII.

Part 4: Construction of pNF034 Containing the Gene Cassette:

The yeast—*E. coli* shuttle vector YEp351 containing the LEU2 marker gene was linearized by digesting it with BamHI. The gene cassette obtained by digesting the recombinant pBSKS vector (achieved through steps described in Example 1, part 3) with BamHI and BglII was ligated into the BamHI site of linearized YEp351. The resultant recombinant expression plasmid containing the gene cassette was designated as pNF034.

Example 2

Transformation of Yeast with pNF034

*Saccharomyces cerevisiae* strain W303 (MATa/MATalpha {leu2-3, 112 trp1-1 can 1-100 ura 3-1 ade 2-1 his 3-11,15} [phi+] was obtained from ATCC (No. 200060) and transformed with pNF034 endowed with the gene cassette. Transformation was conducted as described by Gietz and Woods (2004) with minor modifications. The procedure involved culturing yeast cells to a density of ~1.2×10$^7$ per ml in a medium made of 2% yeast extract, 4% peptone and 4% dextrose containing 10 mg % adenine hemisulphate. The cells were subjected to heat shock in transformation mix containing 0.1 M lithium acetate, 100 µg salmon sperm DNA and 33.3% polyethylene glycol at 42° C. for 180 minutes. Washed cells were plated on synthetic medium devoid of leucine in order to select transformants by leucine auxotrophic mutation and wild type gene complementation at the end of 48-hour incubation at 28±2° C. (Rose 1987a). Simultaneously, the parent yeast strain was also transformed with YEp351 alone to serve as control. Recombinant plasmids were isolated from yeast transformants as per the method of Rose (1987b). Restriction digestion with BamHI of recombinant plasmid isolated from transformants resulted in the isolation of the ~10 kb fragment corresponding to the vector containing the gene cassette. The confirmed yeast transformant hosting pNF034 encoding the gene cassette was designated as tNF006.

Example 3

Batch Cultivation of *Saccharomyces cerevisiae*

Pre-cultures of *S. cerevisiae* W303 were made from single colonies in 100 ml of defined medium containing 0.67% yeast nitrogen base, 2% glucose and supplemented with amino acids, uracil and adenine hemisulphate while *S. cerevisiae* tNFOO6 endowed with the gene cassette was cultured from single colonies in the same defined medium omitting leucine. Pre-cultures were obtained by growing the strains in 500 ml Erlenmeyer flasks at 28±2° C., 200 rpm, for 14-16 hours. Equal amount of cells ($5\times10^6$ cells) of both the parent and transformant strains were used for batch cultivation experiments in triplicates. *S. cerevisiae* W303 cells were grown as stationary cultures at 28±2° C. for 48 hours in 650 ml stoppered glass bottles containing 500 ml of fermentation medium made of 0.67% yeast nitrogen base, 10% glucose and supplemented with amino acids, uracil and adenine hemisulphate. Similar media and conditions were used for fermentation of *S. cerevisiae* tNFOO6 but for the omission of leucine in the medium.

Example 4

Methods of Analysis

Part 1: Growth of *Saccharomyces cerevisiae* Strains

Cell densities of the *Saccharomyces cerevisiae* strains mentioned in Example 3 were monitored over the 48-hour growth period at 600 nm in a Shimadzu UV-1601 spectrophotometer (Shimadzu Inc, Kyoto, Japan). Average values obtained from three different experiments are depicted in FIG. 3. Informed scientists can make out from the data that the growth of the parent W303 strain is much lower than that of the tNF006 transformant endowed with the gene cassette. More specifically, the growth attained by the parent strain within 48 hours of growth could be obtained by the transformant within about 8 hours marked by the beginning of the exponential growth phase. Further, the transformant could be cultured to $A_{600}$ of about 3.9 units by the end of 48 hours of growth as compared to 0.5 units obtained in case of the parent strain. This incremental growth of the transformant, which accounted to 8-fold increase as compared to the parent strain, reflected the effect of rapid recycling of redox potential in the strain.

Part 2: Analysis of Glucose Consumption

Glucose consumption by the parent (W303) and transformant (tNF006) *S. cerevisiae* strains was analyzed by determining residual glucose content in the fermentation media at specified time periods and subtracting the obtained value from the initial concentration of glucose (10%) available at the beginning of fermentation. Aliquots of fermentation medium (50 ml) were clarified of yeast cells at specified times by centrifugation at 10,000 rpm for 15 minutes and used for determination of their glucose contents employing 3,5-dinitrosalicylic acid which is converted to orange-yellowish compound by reducing sugars (Miller, 1972). Average values obtained from three different experiments are depicted in FIG. 4. It could be discerned from the data that glucose consumption (g/L) begins at around 9 hours both by the parent W303 as well as by the transformant tNF006 strains. Subsequent consumption of glucose by the transformant strain at the end of 48 hours was rapid and accounted to ~84% consumption of the total glucose available in the medium. This was 76% more of glucose consumed by the transformant as compared to the parent strain at the end of 48 hours of fermentation, reflecting the effect of rapid recycling of redox potential in the transformant strain.

Part 3: Analysis of Alcohol Production

Clarified aliquots of fermentation medium withdrawn at specified times and clarified as described in Example 4, part 3 were estimated for ethanol contents using Shimadzu GC-14B Gas Chromatograph (Shimadzu Inc, Kyoto, Japan) equipped with Flame Ionization Detector (FID) and using Porapak Q column, as per the protocol mentioned by Templeton (1994) with minor modifications. Parameters emploted for estimating ethanol content in 10 µl. samples include Oven Temperature at 140° C., Injection port temperature: at 220° C., FID temperature at 240° C. using nitrogen carrier gas maintained at 225 KPa, Hydrogen at 50 KPa and air at 25 KPa. From the data depicted in FIG. 5, it becomes evident that ethanol production by W303 parent strain of *S. cerevisiae* started at 36 hours. Contrarily, ethanol production by the tNF006 transformant commenced at an early time period of 6 hours to reach a maximum of ~40 g/L at the end of a 48-hour fermentation period. The parent W303 strain could produce only ~4 g of ethanol/L at the end of this fermentation period. This 10-fold increase in total ethanol production by the transformant at the end of 48 hrs reflected the increased recycling of the redox potential contributing to the excessive production of ethanol by the transformant containing the gene cassette.

Part 4: Evaluating Stoichiometric Relations Between Substrate Consumption and Product Formation FIG. 6 depicts a detailed comparison of the stoichiometric conversion of substrate (Glucose) to product (Ethanol) between W303 parent and its transformant revealed: (i) ethanol production from glucose by the transformant was evident within the first 6 hours of fermentation (ii) the rate at which glucose could be converted to ethanol by the parent W303 strain in 48 hours was achieved by the transformant within 9 hours of fermentation (iii) considering that the theoretical maximum of Glucose conversion to Ethanol (2 moles Ethanol per mole of Glucose), such a relation could be achieved by the transformant tNF006 by the end of 36 hours. This indicated that rapid recycling of reduction potential positively influences the rate of ethanol production.

Example 5

Enzyme Assays

Part 1: Assay of Glyceraldehyde 3-Phosphate Dehydrogenase Activity

In order to confirm the overexpression of TDH3 resident in the gene cassette within the transformant strain, glyceraldehyde 3-phosphate dehydrogenase activity was assayed. Cell free extracts were made from the parent W303 and transformant tNF006 strains of *S. cerevisiae* in 0.1M phosphate buffer, pH 7.5 containing 2 mM $MgCl_2$ and 1 mM dithiothreitol as per van Hoek (2000) and assayed for the enzyme as described by Worthington (1993). FIG. 7 depicts data obtained in this regard and demonstrates that the activity of the enzyme was significantly enhanced ranging from 2.3 fold increase observed at 3 hour growth period to about 6.3 fold increase observed at the end of 48 hours of fermentation. In case of the transformant, the specific activity of the enzyme increased form a value of about 8.5 at 6 hours to about 20 at 36 hours.

Part 2: Assay of Alcohol Dehydrogenase Activity

In order to confirm the overexpression of ADH1 resident in the gene cassette within the transformant strain, the activity of alcohol dehydrogenase was assayed. Cell free extracts were made from the parent W303 and transformant tNF006 strains of *S. cerevisiae* in 0.1M phosphate buffer, pH 7.5 containing 2 mM $MgCl_2$ and 1 mM dithiothreitol as per van Hoek (2000) and assayed for the activity of alcohol dehydrogenase as per the method described by Valle (1955). FIG. 8 depicts data in this regard and demonstrates that the activity of ADH enzyme was significantly enhanced by about 3.5 folds in transformant as opposed to W303 parent at the end of 48 hours of fermentation. The enzyme activity of the transformant increase as the time progressed and hence the specific activity of about 17 (mmol NADH oxidized/min./mg. protein) at 3 hrs to about 169 by 48 hours, showing about 10 fold increase in activity in 48 hours of fermentation.

Deposited Microorganisms

The following microorganisms were deposited with MTCC Microbial Type Culture Collection & Gene Bank, on 11 Dec. 2008, at Institute of Microbial Technology, Sector 39-A, Chandigarh—160 036, INDIA, under the rules of the Budapest Treaty.

| Microorganism | Strain Designation | Accession Number |
|---|---|---|
| Diploid strain of Saccharomyces cerevisiae | tNF 006 | MTCC5451 |

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a biosynthetic intermediate" includes a plurality of such intermediates, reference to "a nucleic acid" includes a plurality of such nucleic acids and reference to "the genetically modified host cell" includes reference to one or more genetically-modified host cells and equivalents thereof known to those skilled in the art and so forth.

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the disclosure(s), specific examples of appropriate materials and methods are described herein. All publications mentioned herein are incorporated herein by reference to disclose and describe the methods and/or materials in connection with which the publications are cited.

The examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

While specific embodiments of the subject disclosures are explicitly disclosed herein, the above specification and examples herein are illustrative and not restrictive. It will be understood that various modifications may be made without departing from the spirit and scope of the disclosure. Many variations of the disclosures will become apparent to those skilled in the art upon review of this specification and the embodiments below. The full scope of the disclosures should be determined by reference to the embodiments, along with their full scope of equivalents and the specification, along with such variations. Accordingly, other embodiments are within the scope of the following claims.

REFERENCES CITED

Patent Documents

| U.S. Pat. No. | 7,091,014 B1 | August 2006 | Aristidou et al |
|---|---|---|---|
| US Patent application | 0,257,983 A1 | November 2006 | Bro et al |
| US Patent application | 0,009,034 A1 | January 2008 | San et al |
| US Patent application | 4,766,071 | August 1988 | Simon et al |
| US Patent application | 5,264,092 | October 1993 | Skotheim et al |
| US Patent application | 5,393,615 | February 1995 | Corey et al |

Other Publications

Baldoma L and Aguilar J. Metabolism of L-fucose and L-rhamnose in *Escherichia coli*: aerobic-anaerobic regulation of L-lactaldehyde dissimilation. J. Biotechnol. 1988, 170: 416-421.

Foster J. W. et al., Regulation of NAD metabolism in *Salmonella typhimurium*: Molecular sequence analysis of the bifunctional nadR regulator and the nadA-pnuC operon. J. Bacteriol. 1990. 172: 4187-4196.

Gietz R. D. and Woods R. A. Transformation of yeast by lithium acetate/single-stranded carrier DNA/polyethylene glycol method. Meth. Enzymol. 2004, 350: 87-96.

Graef M. R. et al., The steady-state internal redox state (NADH/NAD) reflects the external redox state and is correlated with catabolic adaptation in *Escherichia coli*. J. Bacteriol. 1999. 181: 2351-2357.

Leonardo M. R. et al. Role of NAD in regulating the adh E gene of *Escherichia coli*. J. Bacteriol., 1996, 178: 6013-6018.

Lopez De Felipe, F et al. Cofactor engineering: A novel approach to metabolic engineering in *Lactococcus lactis* by controlled expression of NADH oxidase. J. Bacteriol., 1998, 180: 3804-3808.

Maestre O et al. Effects of ADH2 overexpression in *Saccharomyces bayanus* during alcohol fermentation. Appl. Environ. Microbiol., 2008, 74: 702-707.

Michnik S. et al. Modulation of glycerol and ethanol yields during alcoholic fermentation in *Saccharomyces cerevisiae* strains overexpressed or disrupted for GPD1 encoding glycerol 3-phosphate dehydrogenase. Yeast. 1998, 13: 783-793.

Miller G. I. Use of dinitrosalicylic acid reagent for determination of reducing sugars. Anal. Chem. 1972, 31: 426-428.

Nevoigt E. et al. Reduced pyruvate decarboxylase and increase glycerol phosphate dehydrogenase [$NAD^+$] levels enhance glycerol production in *Saccharomyces cerevisiae*. Yeast. 1998, 12: 1331-1337.

Nissen T. L. et al. Optimization of ethanol production in *Saccharomyces cerevisiae* by metabolic engineering of the ammonium assimilation. Metabol. Engg. 2000, 2: 69-77.

Ostrander D. B. et al. Effect of CTP synthase regulation by CTP on phospholipids synthesis in *Saccharomyces cerevisiae*. J. Biol. Chem. 1998, 273: 18992-19001.

Remize F. et al. Glycerol overproduction by engineered *Saccharomyces cerevisiae* wine yeast strains leads to substantial changes in by-product formation and to a stimulation of fermentation rate in stationary phase. Appl. Environ. Microbiol. 1999, 65: 143-149. Roberts G. G. et al. Transcriptome profiling of *Saccharomyces cerevisiae* during a transition from fermentative to glycerol-based respiratory growth reveals extensive metabolic and structural remodeling. Mol. Genet. Genomics 2006. 276: 170-186

Rose M. D. Isolation of genes by complementation in yeast Meth. Enzymol. 1987a, 152: 481

Rose M. D. Isolation of genes by complementation in yeast. Meth. Enzymol. 1987b, 152: 499-500.

Sanchez A. M. et al. Effect of different levels of NADH availability on metabolic fluxes of *E. coli* chemostat cultures in defined medium. J. Biotechnol. 2005, 117: 395-405.

Sastry P. S. and Rao K. S., Apoptosis and the nervous system. Journal of Neurochemistry 2000, 74 (1): 1-20

Templeton D. W. Determination of ethanol concentration in biomass to ethanol fermentation supernatants by gas chromatography. NREL Laboratory analytical protocol # LAP 011, 5-5-1994

Valadi H. et al. NADH reductive stress in *Saccharomyces cerevisiae* induces the expression of minor isoform of Triosephosphate Dehydrogenase 1. Curr. Genet. 2005. 45: 90-95

Vallee B. L. Zinc, a component of yeast alcohol dehydrogenase. Proc. Natl. Acad. Sci USA 1955, 41: 327-337.

Van Hoek P. et al Regulation of fermentative capacity and levels of glycolytic enzymes in chemostat cultures of *Saccharomyces cerevisiae*. Enzyme and Microbial Technology. 2000, 26: 724-736.

Worthington, V. Glyceraldehyde 3-phosphate dehydrogenase. Worthington Enzyme Manual. Worthington Biochemical Corporation. New Jersey, USA. 1993, pp 201-206

---

We claim:

1. A gene cassette construction comprising a Triosephosphate dehydrogenase (TDH3) gene from *Saccharomyces cerevisiae* driven by a first *Saccharomyces cerevisiae* ADH1 promoter followed by an Alcohol dehydrogenase (ADH1) gene from *Saccharomyces cerevisiae* driven by a second *Saccharomyces cerevisiae* ADH1 promoter.

2. The gene cassette construction according to claim 1, wherein the genes are positioned in tandem.

3. The gene cassette construction according to claim 1, wherein the gene cassette is multimerized.

4. A yeast host strain comprising the gene cassette construction according to claim 1, wherein the genes are introduced into host yeast strains either as episomal or chromosomal integrates.

5. A yeast host strain comprising the gene cassette construction according to claim 1, wherein the gene cassette is introduced into host yeast strains for the production of ethanol, lactic acid and other fermentative products.

6. A yeast host strain comprising the gene cassette construction according to claim 1, wherein the genes are introduced into *Saccharomyces cerevisiae* haploid, diploid or polyploid strains.

7. A method comprising:
   transforming any host yeast strain for the utilization of glucose as a carbon source using the gene cassette construction according to claim 1.

8. A method comprising:
   transforming any host yeast strain for the utilization of any monosaccharide as a carbon source, using the gene cassette construction according to claim 1.

9. The gene cassette construction according to claim 1, wherein the genes are separated by a non-transcribable sequence which is not less than 50 and not more than 200 base pairs.

* * * * *

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caccaagaac ttagtttcg                                                       19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccccaaaatt attaagagcg cc                                                   22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcccccgtt gttgtctcac c                                                    21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 4
ggcatttgct cggcatgccg g                                        21

<210> SEQ ID NO 5
<211> LENGTH: 4451
<212> TYPE: DNA
<213> ORGANISM: Saccharomyces cerevisiae
<220> FEATURE:
<223> OTHER INFORMATION: ADH-TDH gene cassette polynucleotide
<220> FEATURE:
<221> NAME/KEY: CDS
<222> LOCATION: (1560)..(2555)
<220> FEATURE:
<221> NAME/KEY: CDS
<222> LOCATION: (3194)..(4237)

<400> SEQUENCE: 5

```
ggatccggga tcgaagaaat gatggtaaat gaaataggaa atcaaggagc atgaaggcaa      60
aagacaaata taagggtcga acgaaaaata aagtgaaaag tgttgatatg atgtatttgg     120
ctttgcggcg ccgaaaaaac gagtttacgc aattgcacaa tcatgctgac tctgtggcgg     180
acccgcgctc ttgccggccc ggcgataacg ctgggcgtga ggctgtgccc ggcggagttt     240
tttgcgcctg cattttccaa ggtttaccct gcgctaaggg gcgagattgg agaagcaata     300
agaatgccgg ttggggttgc gatgatgacg accacgacaa ctggtgtcat tatttaagtt     360
gccgaaagaa cctgagtgca tttgcaacat gagtatacta gaagaatgag ccaagacttg     420
cgagacgcga gtttgccggt ggtgcgaaca atagagcgac catgaccttg aaggtgagac     480
gcgcataacc gctagagtac tttgaagagg aaacagcaat agggttgcta ccagtataaa     540
tagacaggta catacaacac tggaaatggt tgtctgtttg agtacgcttt caattcattt     600
gggtgtgcac tttattatgt tacaatatgg aagggaactt tacacttctc ctatgcacat     660
atattaatta aagtccaatg ctagtagaga agggggtaa cacccctccg cgctctttc     720 cgattttttt ctaaaccgtg gaatatttcg gatatccttt tgttgtttcc gggtgtacaa     780
tatggacttc ctctttttctg caaccaaac ccatacatcg ggattcctat aataccttcg     840
ttggtctccc taacatgtag gtggcggagg ggagatatac aatagaacag ataccagaca     900
agacataatg ggctaaacaa gactacacca attacactgc ctcattgatg gtggtacata     960
acgaactaat actgtagccc tagacttgat agccatcatc atatcgaagt ttcactaccc    1020 ttttccatt tgccatctat tgaagtaata ataggcgcat gcaacttctt ttcttttttt    1080 ttctttctc tctccccgt tgttgtctca ccatatccgc aatgacaaaa aaatgatgga    1140
agacactaaa ggaaaaaatt aacgacaaag acagcaccaa cagatgtcgt tgttccagag    1200
ctgatgaggg gtatctcgaa gcacacgaaa ctttttcctt ccttcattca cgcacactac    1260
tctctaatga gcaacggtat acggccttcc ttccagttac ttgaatttga aataaaaaaa    1320
agtttgctgt cttgctatca agtataaata gacctgcaat tattaatctt ttgtttcctc    1380
gtcattgttc tcgttccctt tcttccttgt ttctttttct gcacaatatt tcaagctata    1440
ccaagcatac aatcaactcc aagcttcgag cggccgcata tgctagctaa gctctagacc    1500
aagaacgcgt ctgcagcacc aagaacttag tttcgaataa acacacataa acaaacaaa     1559
```

| atg | gtt | aga | gtt | gct | att | aac | ggt | ttc | ggt | aga | atc | ggt | aga | ttg | gtc | 1607 |
|-----|-----|-----|-----|-----|-----|-----|-----|-----|-----|-----|-----|-----|-----|-----|-----|------|
| Met | Val | Arg | Val | Ala | Ile | Asn | Gly | Phe | Gly | Arg | Ile | Gly | Arg | Leu | Val |      |
| 1   |     |     |     | 5   |     |     |     |     | 10  |     |     |     |     | 15  |     |      |

| atg | aga | att | gct | ttg | tct | aga | cca | aac | gtc | gaa | gtt | gtt | gct | ttg | aac | 1655 |
|-----|-----|-----|-----|-----|-----|-----|-----|-----|-----|-----|-----|-----|-----|-----|-----|------|
| Met | Arg | Ile | Ala | Leu | Ser | Arg | Pro | Asn | Val | Glu | Val | Val | Ala | Leu | Asn |      |
|     |     |     |     | 20  |     |     |     |     | 25  |     |     |     |     | 30  |     |      |

```
gac cca ttc atc acc aac gac tac gct gct tac atg ttc aag tac gac    1703
Asp Pro Phe Ile Thr Asn Asp Tyr Ala Ala Tyr Met Phe Lys Tyr Asp
         35                  40                  45 tcc act cac ggt aga tac gct ggt gaa gtt tcc cac gat gac aag cac    1751
Ser Thr His Gly Arg Tyr Ala Gly Glu Val Ser His Asp Asp Lys His
     50                  55                  60 atc att gtc gat ggt aag aag att gct act tac caa gaa aga gac cca    1799
Ile Ile Val Asp Gly Lys Lys Ile Ala Thr Tyr Gln Glu Arg Asp Pro
65                  70                  75                  80 gct aac ttg cca tgg ggt tct tcc aac gtt gac atc gcc att gac tcc    1847
Ala Asn Leu Pro Trp Gly Ser Ser Asn Val Asp Ile Ala Ile Asp Ser
                 85                  90                  95 act ggt gtt ttc aag gaa tta gac act gct caa aag cac att gac gct    1895
Thr Gly Val Phe Lys Glu Leu Asp Thr Ala Gln Lys His Ile Asp Ala
            100                 105                 110 ggt gcc aag aag gtt gtt atc act gct cca tct tcc acc gcc cca atg    1943
Gly Ala Lys Lys Val Val Ile Thr Ala Pro Ser Ser Thr Ala Pro Met
        115                 120                 125 ttc gtc atg ggt gtt aac gaa gaa aaa tac act tct gac ttg aag att    1991
Phe Val Met Gly Val Asn Glu Glu Lys Tyr Thr Ser Asp Leu Lys Ile
    130                 135                 140 gtt tcc aac gct tct tgt acc acc aac tgt ttg gct cca ttg gcc aag    2039
Val Ser Asn Ala Ser Cys Thr Thr Asn Cys Leu Ala Pro Leu Ala Lys
145                 150                 155                 160 gtt atc aac gat gct ttc ggt att gaa gaa ggt ttg atg acc act gtc    2087
Val Ile Asn Asp Ala Phe Gly Ile Glu Glu Gly Leu Met Thr Thr Val
                165                 170                 175 cac tct ttg act gct act caa aag act gtt gac ggt cca tcc cac aag    2135
His Ser Leu Thr Ala Thr Gln Lys Thr Val Asp Gly Pro Ser His Lys
            180                 185                 190 gac tgg aga ggt ggt aga acc gct tcc ggt aac atc atc cca tcc tcc    2183
Asp Trp Arg Gly Gly Arg Thr Ala Ser Gly Asn Ile Ile Pro Ser Ser
        195                 200                 205 acc ggt gct gct aag gct gtc ggt aag gtc ttg cca gaa ttg caa ggt    2231
Thr Gly Ala Ala Lys Ala Val Gly Lys Val Leu Pro Glu Leu Gln Gly
210                 215                 220 aag ttg acc ggt atg gct ttc aga gtc cca acc gtc gat gtc tcc gtt    2279
Lys Leu Thr Gly Met Ala Phe Arg Val Pro Thr Val Asp Val Ser Val
225                 230                 235                 240 gtt gac ttg act gtc aag ttg aac aag gaa acc acc tac gat gaa atc    2327
Val Asp Leu Thr Val Lys Leu Asn Lys Glu Thr Thr Tyr Asp Glu Ile
                245                 250                 255 aag aag gtt gtt aag gct gcc gct gaa ggt aag ttg aag ggt gtt ttg    2375
Lys Lys Val Val Lys Ala Ala Ala Glu Gly Lys Leu Lys Gly Val Leu
            260                 265                 270 ggt tac acc gaa gac gct gtt gtc tcc tct gac ttc ttg ggt gac tct    2423
Gly Tyr Thr Glu Asp Ala Val Val Ser Ser Asp Phe Leu Gly Asp Ser
        275                 280                 285 cac tct tcc atc ttc gat gct tcc gct ggt atc caa ttg tct cca aag    2471
His Ser Ser Ile Phe Asp Ala Ser Ala Gly Ile Gln Leu Ser Pro Lys
        290                 295                 300 ttc gtc aag ttg gtc tcc tgg tac gac aac gaa tac ggt tac tct acc    2519
Phe Val Lys Leu Val Ser Trp Tyr Asp Asn Glu Tyr Gly Tyr Ser Thr
305                 310                 315                 320 aga gtt gtc gac ttg gtt gaa cac gtt gcc aag gct taagtgaatt        2565
Arg Val Val Asp Leu Val Glu His Val Ala Lys Ala
                325                 330 tactttaaat cttgcattta aataaatttt cttttatag ctttatgact tagtttcaat  2625
ttatatacta ttttaatgac attttcgatt cattgattga aagctttgtg ttttttcttg 2685
```

-continued

```
atgcgctatt gcattgttct tgtcttttc gccacatgta atatctgtag tagatacctg    2745
atacattgtg gatgctgagt gaaattttag ttaataatgg aggcgctctt aataattttg    2805
gggagatccc tcccccgttg ttgtctcacc atatccgcaa tgacaaaaaa atgatggaag    2865
acactaaagg aaaaaattaa cgacaaagac agcaccaaca gatgtcgttg ttccagagct    2925
gatgaggggt atctcgaagc acacgaaact ttttccttcc ttcattcacg cacactactc    2985
tctaatgagc aacggtatac ggccttcctt ccagttactt gaatttgaaa taaaaaaag    3045 tttgctgtct tgctatcaag tataaataga cctgcaatta ttaatctttt gtttcctcgt    3105
cattgttctc gttcccttc ttccttgttt ctttttctgc acaatatttc aagctatacc    3165
aagcatacaa tcaactatct catattca atg tct atc cca gaa act caa aaa       3217
                                 Met Ser Ile Pro Glu Thr Gln Lys
                                         335             340 ggt gtt atc ttc tac gaa tcc cac ggt aag ttg gaa tac aaa gat att      3265
Gly Val Ile Phe Tyr Glu Ser His Gly Lys Leu Glu Tyr Lys Asp Ile
                345                 350                 355 cca gtt cca aag cca aag gcc aac gaa ttg ttg atc aac gtt aaa tac      3313
Pro Val Pro Lys Pro Lys Ala Asn Glu Leu Leu Ile Asn Val Lys Tyr
        360                 365                 370 tct ggt gtc tgt cac act gac ttg cac gct tgg cac ggt gac tgg cca      3361
Ser Gly Val Cys His Thr Asp Leu His Ala Trp His Gly Asp Trp Pro
    375                 380                 385 ttg cca gtt aag cta cca tta gtc ggt ggt cac gaa ggt gcc ggt gtc      3409
Leu Pro Val Lys Leu Pro Leu Val Gly Gly His Glu Gly Ala Gly Val
390                 395                 400 gtt gtc ggc atg ggt gaa aac gtt aag ggc tgg aag atc ggt gac tac      3457
Val Val Gly Met Gly Glu Asn Val Lys Gly Trp Lys Ile Gly Asp Tyr
405                 410                 415                 420 gcc ggt atc aaa tgg ttg aac ggt tct tgt atg gcc tgt gaa tac tgt      3505
Ala Gly Ile Lys Trp Leu Asn Gly Ser Cys Met Ala Cys Glu Tyr Cys
                425                 430                 435 gaa ttg ggt aac gaa tcc aac tgt cct cac gct gac ttg tct ggt tac      3553
Glu Leu Gly Asn Glu Ser Asn Cys Pro His Ala Asp Leu Ser Gly Tyr
            440                 445                 450 acc cac gac ggt tct ttc caa caa tac gct acc gct gac gct gtt caa      3601
Thr His Asp Gly Ser Phe Gln Gln Tyr Ala Thr Ala Asp Ala Val Gln
        455                 460                 465 gcc gct cac att cct caa ggt acc gac ttg gcc caa gtc gcc ccc atc      3649
Ala Ala His Ile Pro Gln Gly Thr Asp Leu Ala Gln Val Ala Pro Ile
    470                 475                 480 ttg tgt gct ggt atc acc gtc tac aag gct ttg aag tct gct aac ttg      3697
Leu Cys Ala Gly Ile Thr Val Tyr Lys Ala Leu Lys Ser Ala Asn Leu
485                 490                 495                 500 atg gcc ggt cac tgg gtt gct atc tcc ggt gct gct ggt ggt cta ggt      3745
Met Ala Gly His Trp Val Ala Ile Ser Gly Ala Ala Gly Gly Leu Gly
                505                 510                 515 tct ttg gct gtt caa tac gcc aag gct atg ggt tac aga gtc ttg ggt      3793
Ser Leu Ala Val Gln Tyr Ala Lys Ala Met Gly Tyr Arg Val Leu Gly
            520                 525                 530 att gac ggt ggt gaa ggt aag gaa gaa tta ttc aga tcc atc ggt ggt      3841
Ile Asp Gly Gly Glu Gly Lys Glu Glu Leu Phe Arg Ser Ile Gly Gly
        535                 540                 545 gaa gtc ttc att gac ttc act aag gaa aag gac att gtc ggt gct gtt      3889
Glu Val Phe Ile Asp Phe Thr Lys Glu Lys Asp Ile Val Gly Ala Val
    550                 555                 560 cta aag gcc act gac ggt ggt gct cac ggt gtc atc aac gtt tcc gtt      3937
Leu Lys Ala Thr Asp Gly Gly Ala His Gly Val Ile Asn Val Ser Val
565                 570                 575                 580
```

-continued

| | | | | | | | | | | | | | | | |
|---|---|---|---|---|---|---|---|---|---|---|---|---|---|---|---|
| tcc | gaa | gcc | gct | att | gaa | gct | tct | acc | aga | tac | gtt | aga | gct | aac | ggt | 3985 |
| Ser | Glu | Ala | Ala | Ile | Glu | Ala | Ser | Thr | Arg | Tyr | Val | Arg | Ala | Asn | Gly |
| | | | | 585 | | | | | 590 | | | | | 595 | | acc acc gtt ttg gtc ggt atg cca gct ggt gcc aag tgt tgt tct gat 4033
Thr Thr Val Leu Val Gly Met Pro Ala Gly Ala Lys Cys Cys Ser Asp
            600                    605                    610 gtc ttc aac caa gtc gtc aag tcc atc tct att gtt ggt tct tac gtc 4081
Val Phe Asn Gln Val Val Lys Ser Ile Ser Ile Val Gly Ser Tyr Val
            615                    620                    625 ggt aac aga gct gac acc aga gaa gct ttg gac ttc ttc gcc aga ggt 4129
Gly Asn Arg Ala Asp Thr Arg Glu Ala Leu Asp Phe Phe Ala Arg Gly
            630                    635                    640 ttg gtc aag tct cca atc aag gtt gtc ggc ttg tct acc ttg cca gaa 4177
Leu Val Lys Ser Pro Ile Lys Val Val Gly Leu Ser Thr Leu Pro Glu
645                    650                    655                    660 att tac gaa aag atg gaa aag ggt caa atc gtt ggt aga tac gtt gtt 4225
Ile Tyr Glu Lys Met Glu Lys Gly Gln Ile Val Gly Arg Tyr Val Val
                    665                    670                    675 gac act tct aaa taagcgaatt tcttatgatt tatgattttt attattaaat 4277
Asp Thr Ser Lys
            680 aagttataaa aaaataagt gtatacaaat tttaaagtga ctcttaggtt ttaaaacgaa 4337 aattcttatt cttgagtaac tctttcctgt aggtcaggtt gctttctcag gtatagcatg 4397 aggtcgctct tattgaccac acctctaccg gcatgccgag caaatgccag atct 4451

<210> SEQ ID NO 6
<211> LENGTH: 332
<212> TYPE: PRT
<213> ORGANISM: Saccharomyces cerevisiae
<220> FEATURE:
<223> OTHER INFORMATION: ADH-TDH gene cassette polypeptide

<400> SEQUENCE: 6

Met Val Arg Val Ala Ile Asn Gly Phe Gly Arg Ile Gly Arg Leu Val
1               5                   10                  15

Met Arg Ile Ala Leu Ser Arg Pro Asn Val Glu Val Val Ala Leu Asn
                20                  25                  30

Asp Pro Phe Ile Thr Asn Asp Tyr Ala Ala Tyr Met Phe Lys Tyr Asp
            35                  40                  45

Ser Thr His Gly Arg Tyr Ala Gly Glu Val Ser His Asp Asp Lys His
        50                  55                  60

Ile Ile Val Asp Gly Lys Lys Ile Ala Thr Tyr Gln Glu Arg Asp Pro
65                  70                  75                  80

Ala Asn Leu Pro Trp Gly Ser Ser Asn Val Asp Ile Ala Ile Asp Ser
                85                  90                  95

Thr Gly Val Phe Lys Glu Leu Asp Thr Ala Gln Lys His Ile Asp Ala
            100                 105                 110

Gly Ala Lys Lys Val Val Ile Thr Ala Pro Ser Ser Thr Ala Pro Met
        115                 120                 125

Phe Val Met Gly Val Asn Glu Glu Lys Tyr Thr Ser Asp Leu Lys Ile
    130                 135                 140

Val Ser Asn Ala Ser Cys Thr Thr Asn Cys Leu Ala Pro Leu Ala Lys
145                 150                 155                 160

Val Ile Asn Asp Ala Phe Gly Ile Glu Glu Gly Leu Met Thr Thr Val
                165                 170                 175

His Ser Leu Thr Ala Thr Gln Lys Thr Val Asp Gly Pro Ser His Lys
            180                 185                 190

```
Asp Trp Arg Gly Gly Arg Thr Ala Ser Gly Asn Ile Ile Pro Ser Ser
        195                 200                 205

Thr Gly Ala Ala Lys Ala Val Gly Lys Val Leu Pro Glu Leu Gln Gly
    210                 215                 220

Lys Leu Thr Gly Met Ala Phe Arg Val Pro Thr Val Asp Val Ser Val
225                 230                 235                 240

Val Asp Leu Thr Val Lys Leu Asn Lys Glu Thr Thr Tyr Asp Glu Ile
                245                 250                 255

Lys Lys Val Val Lys Ala Ala Ala Glu Gly Lys Leu Lys Gly Val Leu
            260                 265                 270

Gly Tyr Thr Glu Asp Ala Val Val Ser Ser Asp Phe Leu Gly Asp Ser
        275                 280                 285

His Ser Ser Ile Phe Asp Ala Ser Ala Gly Ile Gln Leu Ser Pro Lys
    290                 295                 300

Phe Val Lys Leu Val Ser Trp Tyr Asp Asn Glu Tyr Gly Tyr Ser Thr
305                 310                 315                 320

Arg Val Val Asp Leu Val Glu His Val Ala Lys Ala
                325                 330

<210> SEQ ID NO 7
<211> LENGTH: 348
<212> TYPE: PRT
<213> ORGANISM: Saccharomyces cerevisiae
<220> FEATURE:
<223> OTHER INFORMATION: ADH-TDH gene cassette polypeptide

<400> SEQUENCE: 7

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220
```

-continued

```
Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```